(12) United States Patent
Perring

(10) Patent No.: US 10,357,331 B1
(45) Date of Patent: Jul. 23, 2019

(54) NON-ABRASIVE CLEANING PRODUCTS

(71) Applicant: David A. Perring, Lincoln, IL (US)

(72) Inventor: David A. Perring, Lincoln, IL (US)

( * ) Notice: Subject to any disclaimer, the term of this patent is extended or adjusted under 35 U.S.C. 154(b) by 0 days.

(21) Appl. No.: 15/862,298

(22) Filed: Jan. 4, 2018

Related U.S. Application Data

(60) Continuation of application No. 13/442,159, filed on Apr. 9, 2012, now abandoned, which is a division of application No. 12/772,931, filed on May 3, 2010, now Pat. No. 8,152,929.

(60) Provisional application No. 61/174,765, filed on May 1, 2009.

(51) Int. Cl.
*A61B 90/80* (2016.01)
*B08B 3/08* (2006.01)
*B65D 85/00* (2006.01)
*B08B 1/00* (2006.01)

(52) U.S. Cl.
CPC .............. *A61B 90/80* (2016.02); *B08B 1/006* (2013.01); *B08B 3/08* (2013.01); *B65D 85/70* (2013.01)

(58) Field of Classification Search
CPC ........... A61B 90/80; B08B 1/006; B08B 3/08; B65D 85/70
See application file for complete search history.

(56) References Cited

U.S. PATENT DOCUMENTS

| 3,752,733 | A | * | 8/1973 | Graham | D21H 17/34 156/305 |
|---|---|---|---|---|---|
| 4,683,165 | A | * | 7/1987 | Lindemann | C08F 257/02 442/164 |
| 4,953,250 | A | * | 9/1990 | Brown | A47L 13/19 15/104.94 |
| 7,101,612 | B2 | * | 9/2006 | Lang | A61K 8/0208 156/183 |
| 7,153,791 | B2 | * | 12/2006 | Boylan | D04H 1/587 442/155 |
| 7,247,586 | B2 | * | 7/2007 | Boylan | D04H 1/587 428/424.4 |
| 7,335,613 | B2 | * | 2/2008 | Cottrell | A01N 59/16 442/123 |
| 7,452,547 | B2 | * | 11/2008 | Lambino | A61K 8/0208 401/132 |
| 7,722,589 | B2 | * | 5/2010 | Fitts, Jr. | A41D 13/1209 604/385.22 |
| 7,884,037 | B2 | * | 2/2011 | Sirovatka | A61K 8/0208 442/102 |
| 7,979,946 | B2 | * | 7/2011 | Kister | C09G 1/08 15/104.94 |
| 8,030,226 | B2 | * | 10/2011 | Bradley | B32B 5/26 442/97 |

(Continued)

*Primary Examiner* — Marc Carlson
(74) *Attorney, Agent, or Firm* — Alvin T. Rockhill

(57) ABSTRACT

The subject invention relates to cleaning products that are highly effective in cleaning articles that are susceptible to scratching, scuffing and/or abrasion. More specifically, the present invention relates to cleaning products that are made with a non-abrasive fabric that is comprised of a multitude of non-woven polyester fibers which are bound together with an ethylene-vinyl chloride copolymer binder into the form of a sheet. These cleaning products are highly effective at removing foreign matter from a substrate surface without scratching or scuffing the surface of the substrate. These cleaning products can be used to clean inanimate articles and in cleaning open lesions on humans and animals.

18 Claims, 4 Drawing Sheets

(56) References Cited

U.S. PATENT DOCUMENTS

| | | | |
|---|---|---|---|
| 8,152,929 B1* | 4/2012 | Perring | A47L 13/16 134/42 |
| 2002/0099318 A1* | 7/2002 | Suehr | A61F 13/0273 602/76 |
| 2002/0107495 A1* | 8/2002 | Chen | A61F 13/512 604/365 |
| 2002/0155281 A1* | 10/2002 | Lang | A61K 8/0208 428/337 |
| 2003/0050589 A1* | 3/2003 | McDevitt | A41D 13/087 602/41 |
| 2003/0104966 A1* | 6/2003 | Suazon | A61K 8/0208 510/438 |
| 2003/0135181 A1* | 7/2003 | Chen | A47L 13/16 604/374 |
| 2004/0062798 A1* | 4/2004 | Lukenbach | A61K 8/22 424/465 |
| 2004/0253297 A1* | 12/2004 | Hedges | A61K 8/0208 424/443 |
| 2005/0047961 A1* | 3/2005 | Bains | A01N 59/00 422/37 |
| 2005/0079987 A1* | 4/2005 | Cartwright | A61K 8/0208 510/296 |
| 2005/0129741 A1* | 6/2005 | Kistler | A61K 8/0208 424/443 |
| 2005/0136772 A1* | 6/2005 | Chen | B32B 27/32 442/381 |
| 2005/0226834 A1* | 10/2005 | Lambino | A61K 8/0208 424/70.1 |
| 2005/0266230 A1* | 12/2005 | Hill | A47L 13/16 428/317.9 |
| 2006/0052018 A1* | 3/2006 | Boylan | D04H 1/587 442/158 |
| 2006/0141014 A1* | 6/2006 | Eknoian | A45D 40/00 424/443 |
| 2007/0099813 A1* | 5/2007 | Luizzi | A61K 8/0208 510/438 |
| 2007/0148432 A1* | 6/2007 | Baker | A61L 15/425 428/304.4 |
| 2007/0292705 A1* | 12/2007 | Moncla | C08J 3/12 428/523 |
| 2007/0295465 A1* | 12/2007 | Dyer | A47L 10/16 162/111 |
| 2007/0299410 A1* | 12/2007 | Eknoian | A61K 8/0208 604/289 |
| 2008/0003906 A1* | 1/2008 | Hill | A47L 13/16 442/221 |
| 2008/0076844 A1* | 3/2008 | Van Sumeren | A61L 15/24 521/137 |
| 2008/0145131 A1* | 6/2008 | Kister | A47L 23/10 401/7 |
| 2008/0145664 A1* | 6/2008 | Sirovatka | A61K 8/0208 428/411.1 |
| 2008/0146484 A1* | 6/2008 | Sirovatka | A61K 8/0208 510/405 |
| 2008/0279960 A1* | 11/2008 | Burton | A01N 59/16 424/618 |
| 2009/0035340 A1* | 2/2009 | Landa | A61K 8/0208 424/405 |
| 2009/0246240 A1* | 10/2009 | Holmberg | A01N 25/34 424/409 |
| 2010/0082088 A1* | 4/2010 | Fassih | A61K 9/0009 607/149 |
| 2010/0143652 A1* | 6/2010 | Stockton | A61K 8/0208 428/141 |
| 2010/0147555 A1* | 6/2010 | Laura, Jr. | D04H 3/011 174/137 R |
| 2011/0129645 A1* | 6/2011 | Dyer | A61K 8/0208 428/147 |
| 2012/0137459 A1* | 6/2012 | Privitera | A01N 59/00 15/104.93 |

* cited by examiner

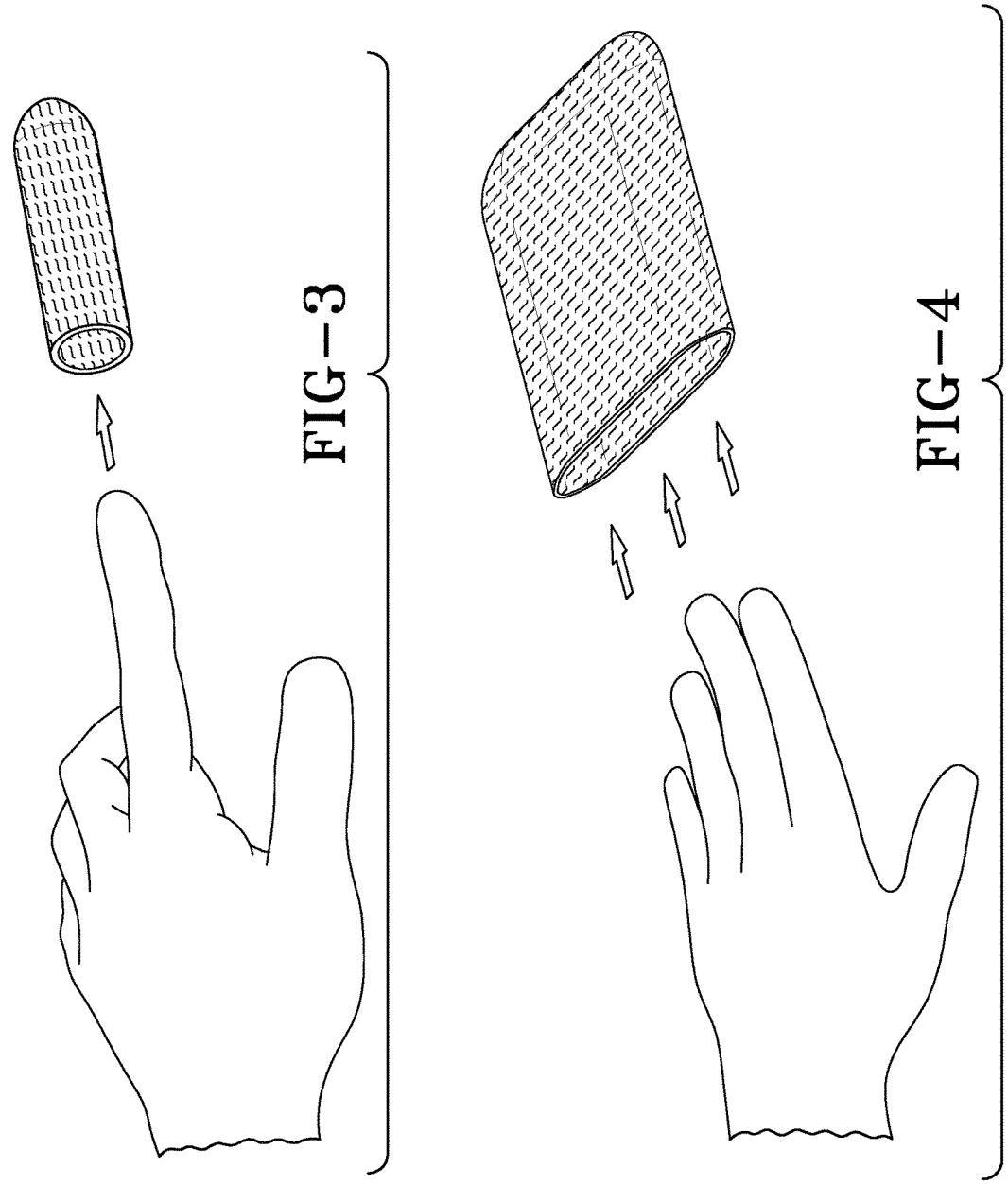

NON-ABRASIVE CLEANING PRODUCTS

This application is a continuation of U.S. patent application Ser. No. 13/442,159, filed on Apr. 9, 2012, which is a divisional and a continuation-in-part of U.S. patent application Ser. No. 12/772,931, filed on May 3, 2010 (now issued as U.S. Pat. No. 8,152,929), which claims the benefit of U.S. Provisional Patent Application Ser. No. 61/174,765, filed on May 1, 2009. The teachings of U.S. patent application Ser. No. 12/772,931 and U.S. Provisional Patent Application Ser. No. 61/174,765 are incorporated herein by reference in their entirety.

BACKGROUND OF THE INVENTION

Cleaning dirt, grime, dust, and other types of foreign matter off articles is an age old problem. This problem is more challenging in cases where the foreign matter adheres tightly to the surface of the "dirty" article and is further complicated in cases where the surface of the article can be scratched in the cleaning process. For instance, cleaning scorched food from the surface of pots and pans can be a difficult proposition. Cleaning burnt food from cooking surfaces is also a commonly encountered problem. Cleaning grime and residual soap scum off fiberglass shower stalls is particularly challenging because cleansers that are abrasive enough to remove the grime and scum will typically scratch the fiberglass surface while milder cleaning products typically prove to be ineffective. Another, common problem is to clean bug residue off the front of motor vehicles. Again, cleaning products that are effective at removing the bug residue can damage the surface of the vehicle if extreme care is not implemented.

Cleaning a dirty wound on humans and animals can be a difficult problem. This is because it is beneficial to minimize further tissue damage to an open lesion. This is often difficult to accomplish in cases where dirt and other foreign matter is present in the open wound. For example, victims of motorcycle accidents typically have multiple cuts and abrasions that can contain various kinds of debris, dirt, small stones, and the like. It is, of course, important to clean foreign matter out of such lesions. However, injuries of this type are normally difficult to thoroughly clean without causing further tissue damage.

Over the years, better cleaning products that are more or less suitable for use in particular situations have been developed. However, cleaning stains, cooked-on grime, and dirt that has a strong affinity for the surface of an article continues to be a problem in the case of surfaces that are susceptible to being scratched or scuffed.

SUMMARY OF THE INVENTION

The subject invention relates to cleaning products that are highly effective in cleaning articles that are susceptible to scratching, scuffing and/or abrasion. More specifically, the present invention relates to cleaning products that are made with a non-abrasive fabric that is comprised of a multitude of non-woven polyester fibers which are bound together with an ethylene-vinyl chloride copolymer binder into the form of a sheet. These cleaning products are highly effective at removing foreign matter from a substrate surface without scratching or scuffing the surface of the substrate. These cleaning products can be use to clean inanimate articles and in cleaning open lesions on humans and animals.

The present invention more specifically discloses a method for cleaning an article which is susceptible to scratching, scuffing and/or abrasion which comprises rubbing the surface of the article with a non-abrasive fabric which is comprised of a multitude of non-woven polyester fibers which are bound together in the form of a sheet with an ethylene-vinyl chloride copolymer binder.

The subject invention further reveals a mitt having a body, a thumb compartment, and a finger compartment wherein said mitt is comprised of a non-abrasive fabric which is comprised of a multitude of non-woven polyester fibers which are bound together in the form of a sheet with an ethylene-vinyl chloride copolymer binder.

The present invention also discloses a finger sleeve which is adapted to fit over a human finger to facilitate the cleaning of animal teeth, animal ears and articles of manufacture wherein said finger sleeve is comprised of a non-abrasive fabric which is comprised of a multitude of non-woven polyester fibers which are bound together in the form of a sheet with an ethylene-vinyl chloride copolymer binder.

The subject invention further discloses a pouch which is adapted to fit over the fingers of a human to facilitate the application of polishes, waxes, cleaners to substrates wherein said pouch is comprised of a non-abrasive fabric which is comprised of a multitude of non-woven polyester fibers which are bound together in the form of a sheet with an ethylene-vinyl chloride copolymer binder.

The present invention also relates to a cleaning pad which is comprised of a front sheet and a back sheet wherein the front sheet and the back sheet are comprised of a non-abrasive fabric which is comprised of a multitude of non-woven polyester fibers which are bound together in the form of a sheet with an ethylene-vinyl chloride copolymer binder, wherein the front sheet and the back sheet are joined together to encapsulated a cleanser within an enclosed area between the front sheet and the back sheet.

The subject invention also reveals a cleaning pad which is comprised of a front sheet and a back sheet wherein the front sheet and the back sheet are comprised of a non-abrasive fabric which is comprised of a multitude of non-woven polyester fibers which are bound together in the form of a sheet with an ethylene-vinyl chloride copolymer binder, wherein the front sheet and the back sheet are joined together to encapsulated a disinfectant within an enclosed area between the front sheet and the back sheet.

The present invention also discloses a cleansing pad having a first side which is comprised of a non-abrasive fabric which is comprised of a multitude of non-woven polyester fibers which are bound together in the form of a sheet with an ethylene-vinyl chloride copolymer binder and a second side which is comprised of terry cloth.

The subject invention further reveals a cleaning towel which is comprised of a top half which is comprised of a non-abrasive fabric which is comprised of a multitude of non-woven polyester fibers which are bound together in the form of a sheet with an ethylene-vinyl chloride copolymer binder and a bottom half is comprised of terry cloth.

The present invention also relates to a wound cleaning cloth kit which is particularly useful for cleaning open wounds in humans and animals while minimizing tissue damage which is comprised of a non-abrasive fabric which is comprised of a multitude of non-woven polyester fibers which are bound together in the form of a sheet with an ethylene-vinyl chloride copolymer binder, wherein the non-abrasive fabric is sterilized, and wherein the non-abrasive fabric is in a sealed pouch that is impervious to penetration by bacteria. In such wound cleaning cloths the non-abrasive fabric can optionally include an antibacterial soap or a cleanser.

In one embodiment of this invention the non-abrasive fabric can be used to implement the cleaning of human hands which are oily, greasy, or generally dirty with conventional cleaning agents, such a soaps or emulsifiers. The non-abrasive fabric of this invention can also be used to facilitate body scrubs on humans or animals. In another embodiment of this invention the non-abrasive fabric can be used in debraiding burns. In still another embodiment of this invention the non-adhesive fabric can be used by the equine industry as leg wraps (either dry or medicated). In a further embodiment of this invention the non-abrasive fabric is used in cleaning canvas, including the canvas used in tents and awnings.

BRIEF DESCRIPTION OF THE DRAWINGS

FIG. 3 illustrates a finger sleeve 6 which is adapted to fit over the form of a human finger 7 to facilitate the cleaning of animal teeth, animal ears and articles of manufacture, wherein the finger sleeve is comprised of the non-abrasive fabric of this invention.

FIG. 4 illustrates a pouch 8 which is adapted to fit over the second finger 9, third finger 10, fourth finger 11 and fifth finger 12 of a human hand 13 wherein the pouch 8 is comprised of the non-abrasive fabric of this invention.

DETAILED DESCRIPTION OF THE INVENTION

Figure 1:
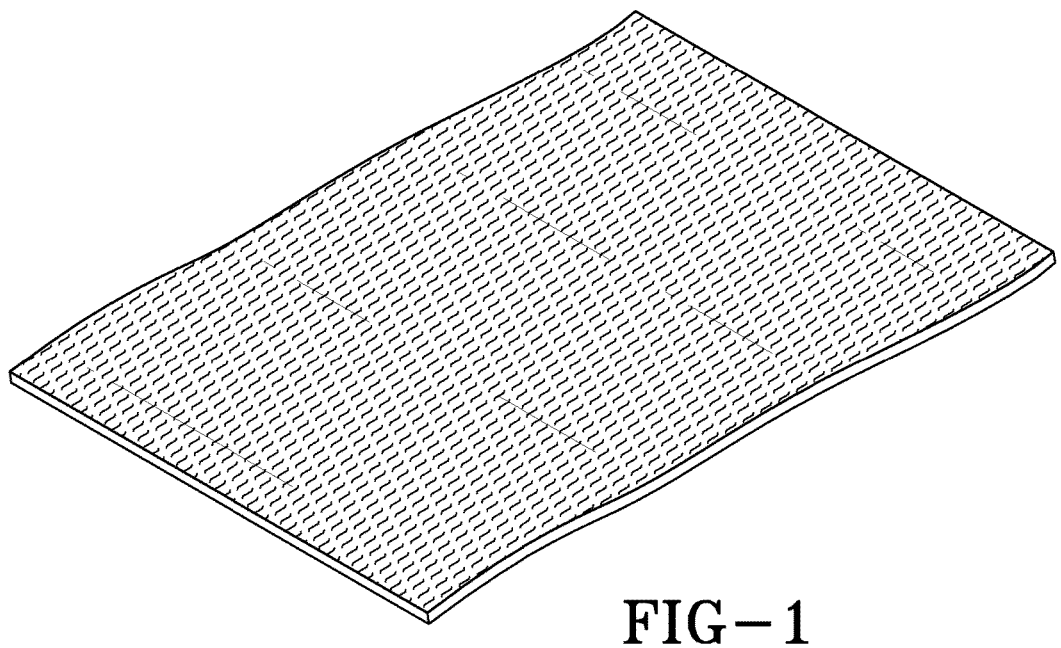
FIG. 1 illustrates a sheet of the non-abrasive fabric of this invention 1 which is comprised of a multitude of non-woven polyester fibers which are bound together in the form of a sheet with an ethylene-vinyl chloride copolymer binder.
Figure 2:
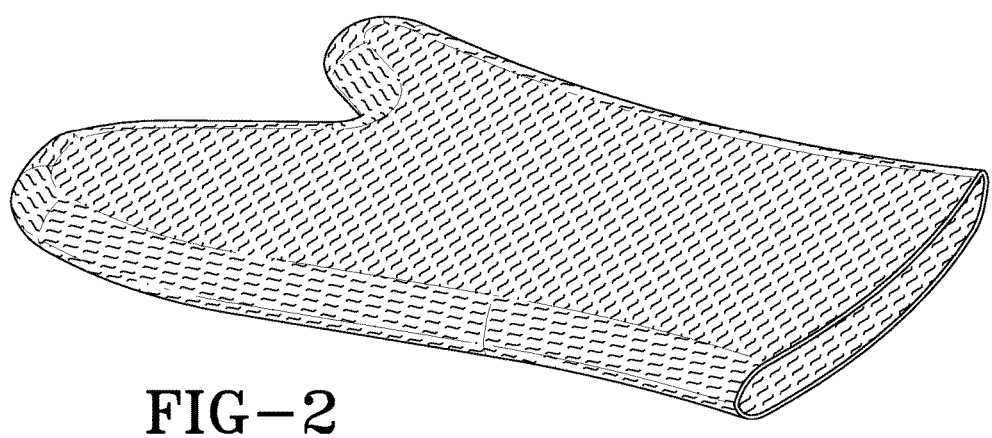
FIG. 2 illustrates a mitt 2 having a body 3, a thumb compartment 4 and a finger compartment 5 which is comprised of the non-abrasive fabric of this invention.
Figure 5:
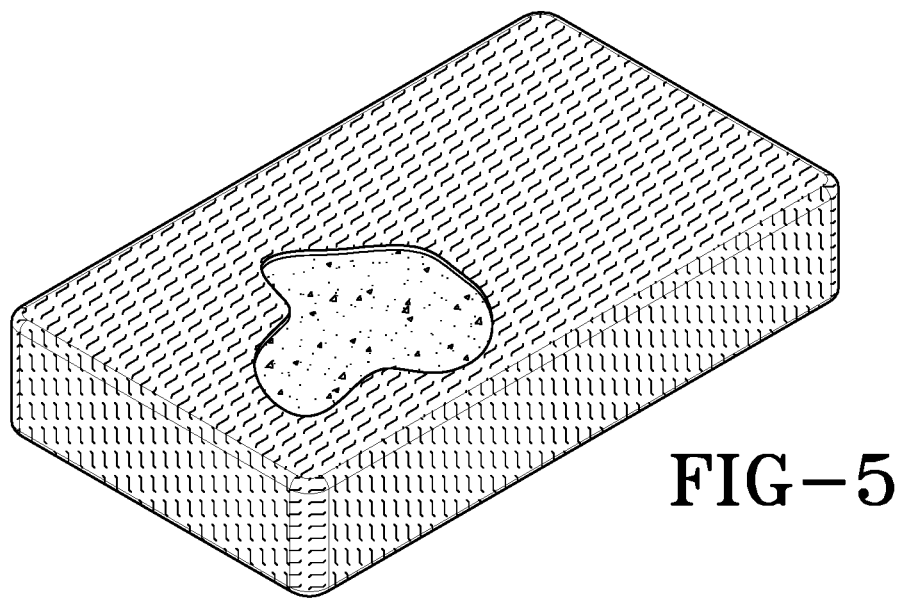
FIG. 5 illustrates a cleaning pad 14 which is comprised of a sponge 16 which is at least partially encapsulated by a non-abrasive fabric 16 which is comprised of a multitude of non-woven polyester fibers which are bound together in the form of a sheet with an ethylene-vinyl chloride copolymer binder, wherein said sponge is impregnated with at least one member of the group consisting of a cleaner, a soap, an emulsifier, a disinfectant, a toothpaste, a wax, and a polish.
Figure 6:
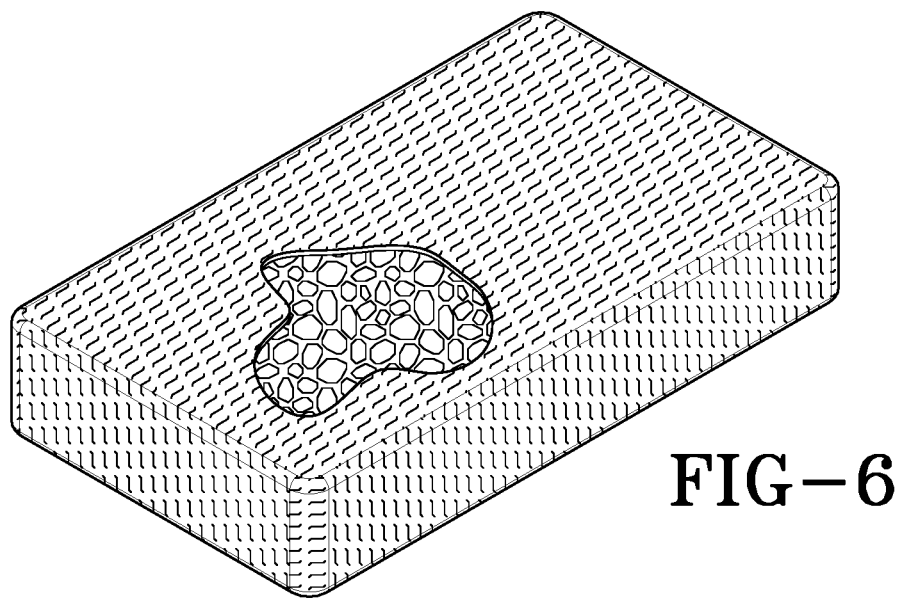
FIG. 6 illustrates a cleaning pad 14 which is comprised of a sponge 15 which is at least partially encapsulated by a non-abrasive fabric 16 which is comprised of a multitude of non-woven polyester fibers which are bound together in the form of a sheet with an ethylene-vinyl chloride copolymer binder.
Figure 7:
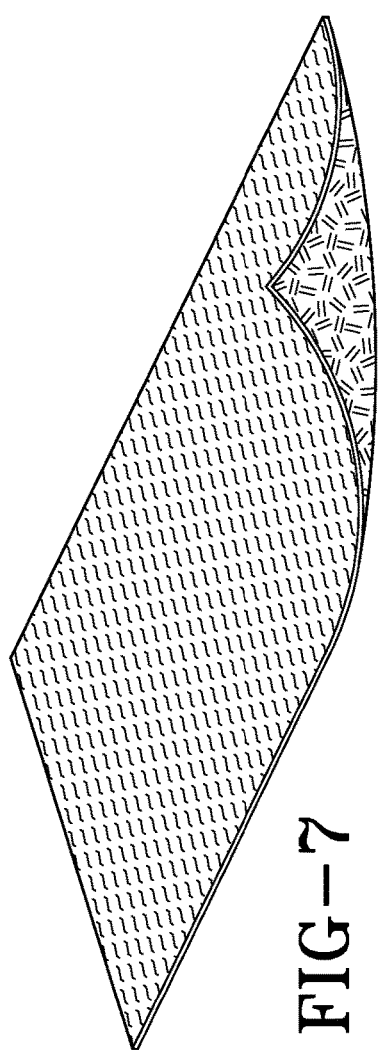
FIG. 7 illustrates a cleaning cloth 17 which has a first side 18 which is comprised of a non-abrasive fabric which is comprised of a multitude of non-woven polyester fibers which are bound together in the form of a sheet with an ethylene-vinyl chloride copolymer binder; and a second side 19 which is comprised of terry cloth.
Figure 8:
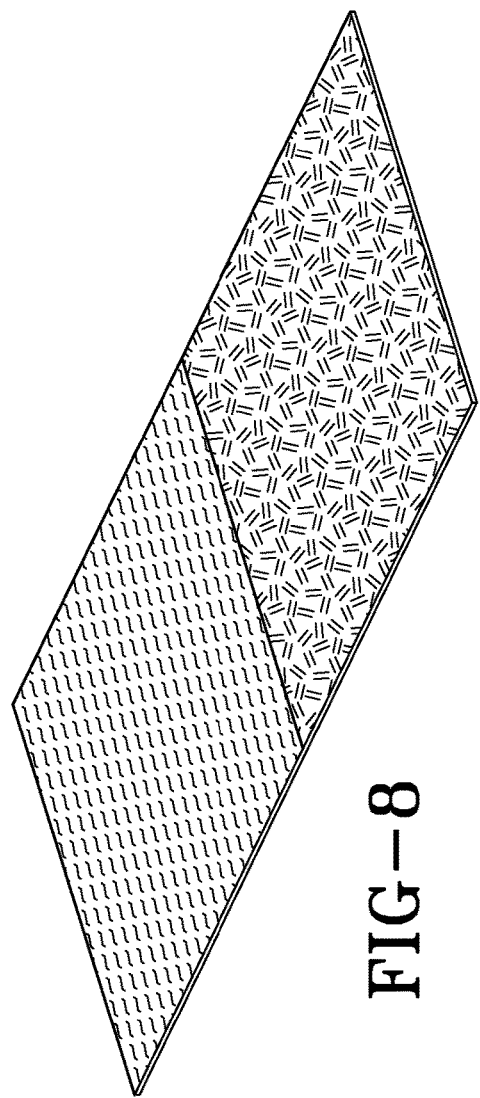
FIG. 8 illustrates a cleaning cloth 20 having a first segment 21 which is comprised of a non-abrasive fabric which is comprised of a multitude of non-woven polyester fibers which are bound together in the form of a sheet with an ethylene-vinyl chloride copolymer binder; and a second segment 22 which is comprised of terry cloth.

The cleaning products of this invention are manufactured utilizing a non-abrasive fabric that is comprised of a multitude of non-woven polyester fibers which are bound together with an ethylene-vinyl chloride copolymer binder into the form of a sheet. The polyester used in making the non-abrasive fabric is typically polyethylene terephthalate or polyethylene naphthalate having an intrinsic viscosity which is within the range of 0.45 dl/g to about 0.85 dl/g. The polyester will more typically have an intrinsic viscosity which is within the range of 0.50 dl/g to about 0.75 dl/g and will normally have an intrinsic viscosity which is within the range of 0.50 dl/g to about 0.70 dl/g. In most cases the polyester will have an intrinsic viscosity which is within the range of 0.55 dl/g to about 0.65 dl/g. It is normally preferred to utilize a polyester having an intrinsic viscosity which is within the range of 0.60 dl/g to about 0.64 dl/g. Polyethylene terephthalate (PET) resins that are useful in the practice of this invention are commercially available from Gruppo Mossi & Ghisolfi and Eastman Chemical. For instance, Cleartuf® P60 PET resin which has an intrinsic viscosity of 0.58 dl/gram, an acetaldehyde content of ≤80 mg/kg, and a melting point of 250° C. can be used in manufacturing the non-woven fabric. Cleartuf® P76 PET resin which has an intrinsic viscosity of 0.74 dl/gram, an acetaldehyde content of 1.0 ppm, and a melting point of 250° C. can optionally be used in manufacturing the non-woven fabric.

The non-abrasive fabric is comprised of a multitude of non-woven polyester fibers which are bound together in the form of a sheet with an ethylene-vinyl chloride copolymer binder. The polyester fibers in the non-woven fabric typically have a diameter which is within the range of about 10 micrometers to about 50 micrometers and more typically have a diameter which is within the range of about 15 micrometers to about 40 micrometers. The polyester fibers will generally have a diameter which is within the range of 20 micrometers to 40 micrometers, such as a diameter which is within the range of 30 micrometers to 40 micrometers. In such cases the polyester fibers can have an average diameter which is within the range of 30 micrometers to 35 micrometers. In most cases the polyester fibers have a diameter which is within the range of about 20 micrometers to about 30 micrometers. It is normally preferred for the polyester fibers have a diameter which is within the range of about 22 micrometers to about 27 micrometers and in some cases it is preferred for the polyester fibers to have a diameter which is within the range of about 30 micrometers to about 38 micrometers.

The non-woven fabric will typically have a density which is within the range of about 0.01 grams/cc to about 0.40 grams/cc and will more typically have a density which is within the range of about 0.02 grams/cc to about 0.30 grams/cc. In most cases the non-abrasive fabric will have a density which is within the range of about 0.03 grams/cc to about 0.20 grams/cc. It is normally preferred for the non-abrasive fabric to have a density which is within the range of about 0.04 grams/cc to about 0.15 grams/cc. It is generally more preferred for the non-abrasive fabric to have a density that is within the range of about 0.05 grams/cc to about 0.10 grams/cc. It is normally most preferred for the non-abrasive fabric to have a density that is within the range of about 0.06 grams/cc to about 0.08 grams/cc.

The ethylene-vinyl chloride polymer (EVC) binder utilized in manufacturing the non-woven fabric can optionally be crosslinked with an external crosslinker, such as melamine or a urea formaldehyde resin to achieve improved wet tensile properties. The use of ethylene-vinyl chloride polymer emulsions as binders for nonwoven fabrics is described in U.S. Pat. No. 7,247,586. The teachings of U.S. Pat. No. 7,247,586 are incorporated herein by reference for the purpose of teachings the types of ethylene-vinyl chloride polymer emulsions that can be used in manufacturing nonwoven fabrics and for the purpose of teaching methods for manufacturing non-woven fabrics with such EVC binders.

The non-woven fabric can be manufactured into a wide variety of products that are useful in specific cleaning applications. For instance, the non-woven fabric can be processed into cleaning mitts, finger sleeves, cleaning pouches, and the like.

This invention is illustrated by the following examples that are merely for the purpose of illustration and are not to be regarded as limiting the scope of the invention or the manner in which it can be practiced. Unless specifically indicated otherwise, parts and percentages are given by weight.

Example 1

A dirty boat hull was cleaned in accordance with the process of this invention utilizing a non-abrasive fabric that was comprised of a multitude of non-woven polyester fibers that were bound together in the form of a sheet with an ethylene-vinyl chloride copolymer binder. It took only a fraction of the time to clean the boat hull than was required to clean it with conventional cleaning products. The non-abrasive fabric of this invention was easy to use and did not scratch the surface of the boat hull. It reduced the amount of time needed to clean the surface of the boat hull and made the cleaning project easier.

Example 2

In this experiment two dinner plates with a residue of Chinese food were left in a sink for 2 days. The residue of the Chinese food was allowed to dry onto the plates for a period of two days. One plate was cleaned using dishwashing liquid and an ordinary sponge. This plate was difficult to clean and required extensive scrubbing and hot water. It took three minutes to effectively clean the entire plate. The second plate was cleaned using the same dishwashing liquid and the non-abrasive fabric and method of the subject invention. This plate was completely clean after approximately one minute of scrubbing time.

Example 3

In this experiment half of a ceramic cooktop range was cleaned with a conventional cooktop cleaner and cleaning pad and the other half was cleaned with the same conventional cleaner but was cleaned in accordance with the process of this invention utilizing a non-abrasive fabric that was comprised of a multitude of non-woven polyester fibers that were bound together in the form of a sheet with an ethylene-vinyl chloride copolymer binder. The entire cooktop was coated with burnt food residue and grease, smudges and mineral deposits. The half of the cooktop surface that was cleaned with the non-abrasive fabric of this invention came much cleaner than the other half because no residue or fingerprints remained and less scrubbing action was needed. It reduced the amount of time needed to clean the surface of the cooktop and made the cleaning project easier. The burnt food residue, grease, water residue, smudges and mineral deposits were removed quickly and easily using the fabric and method of this invention.

Example 4

In this experiment the non-abrasive fabric of this invention was used by nurses to clean a deep, bleeding wound on a person's leg. The non-abrasive fabric was compared to gauze which is what is normally used to clean wounds. The nurses determined that the fabric of this invention cleaned the wound better than conventional gauze because the gauze is slick, slippery and very thin. The gauze was quickly oversaturated and needed to be thrown away and replaced with fresh gauze. Using the non-abrasive fabric of this invention cleaned the wound much faster than conventional gauze because it was more absorbent but gentle on the wound and did not damage human tissue.

Example 5

In this experiment an automobile was cleaned using both conventional car cleaning products and the method and non-abrasive fabric of the present invention. The right side of the car was cleaned using standard automotive wash soap and a sponge and a cloth. The left side of the car was cleaned using standard automotive wash soap and the non-abrasive fabric of the present invention. Using the non-abrasive fabric of the present invention, the left side of the car was easier and faster to clean. The non-abrasive fabric did not scratch the car's surface and also did not leave the swirls on the car's finish as do other conventional car cleaning products. Additional, the non-abrasive fabric more easily removed dead bugs and insects from the windshield of the car because the fabric did not need to get as wet as a sponge to loosen and remove the dead bugs.

Example 6

In this experiment a set of golf clubs was cleaned. Half of the clubs were cleaned using a conventional golf club cleaning kit that includes sponges, a jar of club cleaner, a towel, a groove cleaner and a two-way cleaning brush. The other half of the clubs was cleaned using the same club cleaner but with the non-abrasive fabric of the present invention. The clubs cleaned with the non-abrasive fabric came clean in less time than those using the conventional kit. Because the non-abrasive fabric could be used in place of the sponge, the towel and the cleaning brush, only one product needs to be purchased. The non-abrasive fabric was superior to the towels in cleaning the golf clubs because it is able to get the grime out of the grooves on the composite club head without scratching and also easily removes grass stains from the iron clubs.

Example 7

In this experiment a veterinarian used the non-abrasive fabric of the present invention in preparation for surgery on a dog being neutered in order to compare it to the use of conventional gauze. The non-abrasive fabric was dampened with an antiseptic in order to clean the area to be operated on. As in Example 4, the non-abrasive fabric proved to be much more efficient than using gauze because it was sturdier and more absorbent and less material needed to be used but was also gentle on the animal's skin.

Example 8

In this experiment a white porcelain sink was cleaned using a powdered household cleanser. The sink was severely stained with rust water stains and tea stains which left it brown and dingy. Half of the sink was cleaned utilizing a non-scratch scrub sponge and the other half was cleaned utilizing the non-abrasive fabric of this invention. The side using the fabric of this invention became completely clean with minimal scrubbing while the other side came clean only after several minutes of scrubbing with the sponge.

Example 9

In this experiment mold was conventionally cleaned from wood shingles on the exterior of a home that had been painted with an oil bases paint utilizing a sponge and a 10% solution of bleach in water. The mold was extremely difficult to remove using this procedure and required about 60 minutes of aggressive cleaning to remove the mold from a 10 ft$^2$ section of shingles. An attempt to remove the mold from another section of the shingles was also made using a cotton cloth again using a 10% solution of bleach in water. This technique did not prove to be effective in removing the mold from the wood shingles. Still another attempt to remove the mold was undertaken using a brush having plastic bristles which was designed for the purpose of cleaning the white sidewalls of tires. However, the use of this brush scratched the surface of the paint and proved to be unsatisfactory. Additionally, this plastic brush did not prove to be particularly effective with regard to removing the mold.

The non-abrasive fabric of the present invention was then used to clean the mold from the painted wood shingles. It made the job of cleaning the mold from the shingles very easy. In fact, mold was removed from a 10 ft$^2$ section of shingles utilizing the 10% solution of bleach in water in less than 10 minutes. Thus, the cleaning speed was increase by about 6 times as compared to the time required to clean the shingles with the sponge. The amount of energy required to clean the shingles (pressure applied) was also reduced substantially making the cleaning project much easier and six times faster.

Example 10

About 100 rounds of .45 Auto cartridges were shot through a Ruger® P90™ pistol. Then, a non-abrasive 5 cm by 5 cm fabric patch of this invention was attached to a gun cleaning rod and saturated with Hoppe's No. 9 Solvent. The fabric patch was then pushed through the barrel of the .45 caliber pistol from the breech and out the muzzle with the cleaning patch being worked through the barrel several times. This resulted in the barrel coming perfectly clean without the need to use a brush having wire bristles to remove any residue. After that another 5 cm by 5 cm fabric patch made with the polyester material of this invention was lightly oiled with Hoppe's lubricating oil and the oily patch was pushed through the barrel of the pistol several times to provide it with a light oil coating to prevent rush or corrosion. In any case, the non-abrasive fabric of this invention made cleaning the firearm possible without the use of a brush having wire bristles which would ordinarily be required. This made cleaning the firearm easier and did not subject it to the wire brush which can ultimately lead to unnecessary barrel wear and deterioration of the rifling. Accordingly, the non-abrasive fabric of this invention is highly desirable for use in cleaning firearms, including pistols, revolvers, rifles, and shotguns.

Example 11

After the hands of a worker became very dirty, greasy and oily from servicing a tractor and other farm implements which included coming in contact with oily residue and hydraulic fluid as well as grease, the non-abrasive fabric of this invention was used to facilitate the cleaning of the worker's hands. In this case, the fabric was impregnated with GOJO® citrus/orange oil based hand cleaner and the cleaner soaked fabric was used to clean the worker's hands by scrubbing them with the fabric. This technique yielded excellent results as compared to cleaning with the use of conventional soap and water, including highly abrasive pumice based soaps. More specifically, the worker's hands became cleaner after a much shorter cleaning time. The non-abrasive fabric of this invention also yielded much better results than using the GOJO® citrus/orange oil based hand cleaner alone. After being cleaned, the worker simply dried his hands with a dry cloth without the need for washing with water. Similar results were attained substituting John Deere citrus/orange oil based cleaner.

Example 12

The hands of a painter got splattered with an oil-based paint during a painting project. The non-abrasive fabric of this invention was used to facilitate the cleaning of paint splatters off of the painter's hands. In this case, the fabric was impregnated with a citrus/orange oil based hand cleaner and the cleanser soaked fabric was used to clean the painter's hands by scrubbing them with the fabric. This technique yielded excellent results as compared to cleaning with the use of conventional soap and water, including highly abrasive pumice based soaps. More specifically, the painter's hands became cleaner after a much shorter cleaning time. The non-abrasive fabric of this invention also yielded much better results than using the citrus/orange oil based hand cleaner alone. In fact, equivalent results could not be attained utilizing conventional cleaning techniques without the use of harsh organic solvents such as turpentine.

Example 13

In a household painting project some wall paint was inadvertently splattered on the woodwork and trim present in the room. The non-abrasive fabric of this invention proved to be highly effective at removing the paint splatters without scratching the woodwork and trim. In the procedure used a citrus/orange oil based cleaner was applied to the non-abrasive fabric and then the fabric was simply rubbed on to the paint splatters to easily remove them from the woodwork and trim where they were present. The procedure of this invention is greatly preferred to using highly abrasive products such as sandpaper and/or volatile organic solvents such as turpentine. The non-abrasive fabric of this invention also made the task of removing the paint splatters from the woodwork and trim faster and easier.

While certain representative embodiments and details have been shown for the purpose of illustrating the subject invention, it will be apparent to those skilled in this art that various changes and modifications can be made therein without departing from the scope of the subject invention.

What is claimed is:

1. A method for cleaning an open wound on a human or an animal while minimizing tissue damage, said method comprising cleaning the open wound with a non-abrasive fabric which is comprised of a multitude of non-woven polyester fibers which are bound together in the form of a sheet with a binder which consists of an ethylene-vinyl chloride copolymer binder, wherein the non-woven polyester fibers have a diameter which is within the range of about 10 micrometers to about 50 micrometers, and wherein the non-woven polyester fibers are polyethylene terephthalate fibers or polyethylene naphthalate fibers.

2. The method for cleaning an open wound as specified in claim 1 wherein the open wound is on a human.

3. The method for cleaning an open wound as specified in claim 1 wherein the open wound is on an animal.

4. The method for cleaning an open wound as specified in claim 1 wherein the non-woven polyester fibers are polyethylene terephthalate fibers.

5. The method for cleaning an open wound as specified in claim 1 wherein the non-woven polyester fibers are polyethylene naphthalate fibers.

6. The method for cleaning an open wound as specified in claim 1 wherein the non-woven polyester fibers have a diameter within the range of about 15 micrometers to about 40 micrometers.

7. The method for cleaning an open wound as specified in claim 1 wherein the non-woven polyester fibers have a diameter within the range of about 20 micrometers to about 30 micrometers.

8. The method for cleaning an open wound as specified in claim 1 wherein the non-woven polyester fibers have a diameter within the range of about 22 micrometers to about 27 micrometers.

9. The method for cleaning an open wound as specified in claim 1 wherein the non-woven polyester fibers are manufactured from a polyester having an intrinsic viscosity which is within the range of 0.45 dl/g to about 0.85 dl/g.

10. The method for cleaning an open wound as specified in claim 1 wherein the non-woven polyester fibers are manufactured from a polyester having an intrinsic viscosity which is within the range of 0.50 dl/g to about 0.75 dl/g.

11. The method for cleaning an open wound as specified in claim 1 wherein the non-woven polyester fibers are manufactured from a polyester having an intrinsic viscosity which is within the range of 0.55 dl/g to about 0.65 dl/g.

12. The method for cleaning an open wound as specified in claim 1 wherein the non-woven polyester fibers are manufactured from a polyester having an intrinsic viscosity which is within the range of 0.60 dl/g to about 0.64 dl/g.

13. The method for cleaning an open wound as specified in claim 1 wherein ethylene-vinyl chloride copolymer binder is crosslinked with an external crosslinker.

14. The method for cleaning an open wound as specified in claim 13 wherein the crosslinker is selected from the group consisting of melamine and urea formaldehyde resin.

15. The method for cleaning an open wound as specified in claim 1 wherein the non-abrasive fabric has a density which is within the range of about 0.01 grams/cc to about 0.40 grams/cc.

16. The method for cleaning an open wound as specified in claim 1 wherein the non-abrasive fabric has a density which is within the range of about 0.02 grams/cc to about 0.30 grams/cc.

17. The method for cleaning an open wound as specified in claim 1 wherein the non-abrasive fabric has a density which is within the range of about 0.04 grams/cc to about 0.15 grams/cc.

18. The method for cleaning an open wound as specified in claim 1 wherein the non-abrasive fabric has a density which is within the range of about 0.06 grams/cc to about 0.08 grams/cc.

* * * * *